(12) United States Patent
Halvorsen

(10) Patent No.: US 7,159,602 B2
(45) Date of Patent: Jan. 9, 2007

(54) FLOW-MEASURING VALVE DEVICE AND METHOD

(75) Inventor: Morten Halvorsen, Kristiansand (NO)

(73) Assignee: Rotator AS, Nodeland (NO)

( * ) Notice: Subject to any disclaimer, the term of this patent is extended or adjusted under 35 U.S.C. 154(b) by 4 days.

(21) Appl. No.: 10/497,891

(22) PCT Filed: Nov. 28, 2002

(86) PCT No.: PCT/NO02/00449

§ 371 (c)(1),
(2), (4) Date: Jan. 31, 2005

(87) PCT Pub. No.: WO03/048742

PCT Pub. Date: Jun. 12, 2003

(65) Prior Publication Data

US 2005/0178442 A1    Aug. 18, 2005

(30) Foreign Application Priority Data

Dec. 6, 2001    (NO) .................................. 20015979

(51) Int. Cl.
*E03B 1/00* (2006.01)

(52) U.S. Cl. .............................. 137/1; 137/12; 137/486; 137/487.5; 73/54.09; 73/54.11; 138/42; 138/46; 251/121

(58) Field of Classification Search .................... 137/2, 137/486, 487.5; 73/54.01, 54.09, 54.11; 138/42, 46; 251/120, 121, 126
See application file for complete search history.

(56) References Cited

U.S. PATENT DOCUMENTS

| 4,576,043 | A |   | 3/1986 | Nguyen |
|---|---|---|---|---|
| 4,644,781 | A | * | 2/1987 | Mon .......................... 73/54.05 |
| 4,905,503 | A |   | 3/1990 | Langrick |
| 5,161,406 | A |   | 11/1992 | Heinonen |
| 5,533,549 | A |   | 7/1996 | Sherman |
| 5,736,650 | A |   | 4/1998 | Hiron et al. |
| 6,412,337 | B1 | * | 7/2002 | Arzate et al. ............... 73/54.09 |

FOREIGN PATENT DOCUMENTS

| EP |   | 0 329 354 | 2/1989 |
|---|---|---|---|
| EP | GB | 2 263 172 | 7/1993 |
| EP | GB | 2 317 019 | 3/1998 |
| SU |   | 623 051 | 5/1978 |
| SU |   | 623051 | 5/1978 |

OTHER PUBLICATIONS

Norwegian Search Report for Norway Patent Application No. 2001 5979, Jul. 24, 2002.
International Search Report for Int'l Application No. PCT/NO02/00449, Mar. 7, 2003.

* cited by examiner

*Primary Examiner*—Ramesh Krishnamurthy
(74) *Attorney, Agent, or Firm*—Kusner & Jaffe

(57) ABSTRACT

A flow measuring valve device (1) for fluid, the flow measuring valve (1) comprising a first restriction (48) and a second restriction (76) connected in series with the first restriction (48), the flow rates of said restrictions (48, 76) being unequally dependent on the viscosity of the fluid, and a method for determining the viscosity of the fluid by means of the device.

9 Claims, 4 Drawing Sheets

FLOW-MEASURING VALVE DEVICE AND METHOD

FIELD OF THE INVENTION

This invention relates to a valve for measuring a flow of fluid, more particularly a valve in which the viscosity of the fluid may be determined by means of pressure drop measuring across two restrictions connected in series, the flow rates of the restrictions being unequally dependent on the viscosity of the fluid. The invention also comprises a method for the use of the valve.

BACKGROUND OF THE INVENTION

When petroleum exploration and recovery of petroleum deposits are being carried out, it is necessary under given circumstances to inject chemicals into the well flow from the reservoir. The aim may be to prevent corrosion, formation of hydrates or deposits.

The chemicals in question here are expensive, and it is desirable, also for environmental reasons, for the chemicals to be dosed into the well stream in an amount as accurate as possible.

According to the prior art, in offshore installations, the chemicals are pumped from a floating or fixed offshore installation down to the sea floor through an umbilical, where the chemicals are distributed to the individual wells. To achieve the desired dosing accuracy, adjustable dosing valves are used, adapted for the chemicals in question here.

Prior art dosing valves are provided with accurately adjustable dosing devices and most often also with a flow-meter which allows the dosing amount to be monitored.

The chemicals used are a mixture of fluids, in which the greatest emphasis is laid on making the mixture have a desired chemical composition. Physical properties such as density and viscosity may vary between mixtures having the same chemical composition.

Thus, it is normal that the viscosity of the fluid is not known for the pressure and temperature conditions prevailing at the point of injection, and it is not a simple task either to predetermine the viscosity at the point of injection.

It has turned out that a change in viscosity of the fluid injected, results in a change in the injection flow even when sophisticated dosing valves according to prior art are used.

If restrictions are used, in which the flow is turbulent and thereby less sensitive to variations in the viscosity, it is a problem that the restriction becomes clogged as the restriction opening must be relatively small with the flow rates in question here.

The invention has as its object to remedy the drawbacks of the prior art.

The object is achieved, according to the invention, through the features set out in the description below and in the following Claims.

SUMMARY OF THE INVENTION

A significantly more accurate dosing may be achieved by measuring the viscosity of the injection fluid at the point of injection, and then, on the basis of the measured data, adjusting the control valve to correct for a possible change in viscosity.

In the valve according to the invention, which is placed at the point of injection, which may be on the sea floor, a fluid flow is carried in series through two restrictions, the pressure drops across the restrictions being unequally dependent on the viscosity of the fluid. At the same time the pressure drop across each of the two restrictions is measured. By comparing the pressure drops across the two restrictions with known calibration data for the two restrictions, the viscosity of the fluid in the prevailing pressure and temperature conditions may be determined, the flow rate and mainly also the viscosity being identical through the two restrictions.

By adjusting an adjustable restriction connected in series, the flow rate through the restriction may be corrected until a desired flow rate through the restrictions is achieved.

If a fluid is flowing through a restriction, the following relation applies (In formulas that apply to one restriction a lowered figure is added to the general value symbol. For example, $R_1$ denotes the constant R for the first restriction, whereas $R_2$ denotes the constant R for the second restriction.):

$$Q = R * \Delta P^k * f_1(v)$$

where Q is the flowrate, R is a constant, $\Delta P$ is the pressure drop, f(v) is a function of the kinematic viscosity v, and k is a constant exponent.

By selecting two restrictions with different viscosity functions, for example one restriction, in which there is a laminar form of flow under the prevailing conditions, and another in which there is a turbulent form of flow, a value may be calculated for the viscosity by solving the continuity equation (the flow rate being the same for both restrictions):

$$R_1 * \Delta P_1^{k1} * f_1(v) = Q = R_2 * \Delta P_2^{k2} * f_2(v)$$

Alternatively, by means of iteration, a flow rate may be calculated, which is the same for both restrictions, whereby the prevailing viscosity appears.

By a given viscosity and pressure drop, the flow rate through the restrictions is known, and an adjustable flow resistance may be adjusted until the desired flow rate is achieved.

BRIEF DESCRIPTION OF THE DRAWINGS

In the following is described a non-limiting example of a preferred embodiment which is visualized in the following drawings, in which.

DETAILED DESCRIPTION OF A PREFERRED EMBODIMENT

Figure 1:
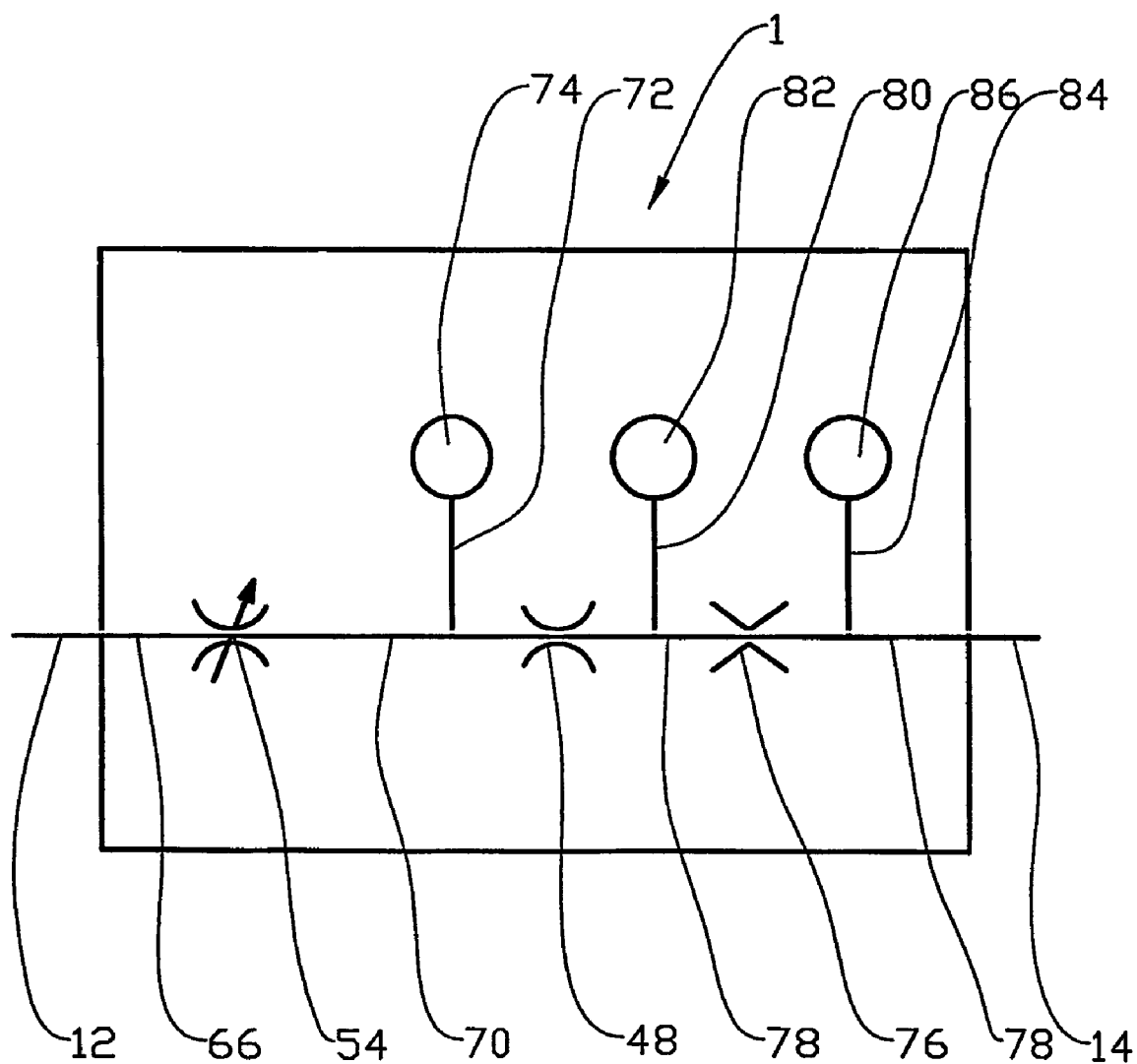
FIG. 1 shows a principle drawing of the valve, the fluid passage of the valve being provided with an adjustable choke valve and two restrictions; manometers being arranged in communication with the passage at the restrictions.
Figure 2:
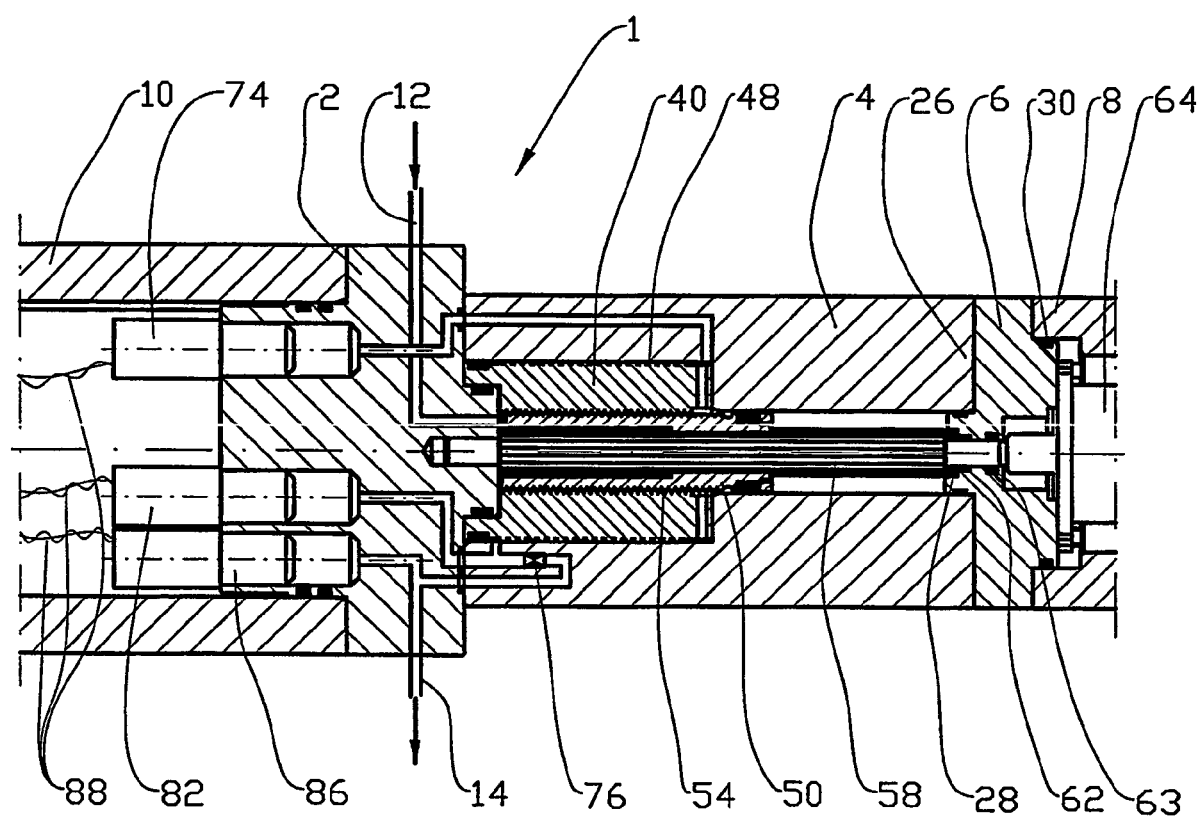
FIG. 2 shows a section through the valve.

In the drawings the reference numeral 1 identifies a flow measuring valve, in the following referred to as a valve, comprising a flanged housing 2, a gauge housing 4, an intermediate plate 6 and a motor bonnet 8 and an instrument bonnet 10.

The flanged housing 2 is provided with an inlet coupling 12 and an outlet coupling 14 for fluid, and is sealingly connected at its first end portion 16 by means of a seal 18 to the instrument bonnet 10. At its second opposite end portion 20 the flanged housing 2 is sealingly connected by means of seals 22 to the first end portion 24 of the gauge housing 4.

The second end portion 26 of the gauge housing 4 is sealingly connected by means of the seals 28 and 30 to the motor bonnet 8 through the intermediate plate 6.

A screw-connection, not shown, is arranged to keep the parts 2, 4, 6, 8 and 10 connected.

The gauge housing 4 is provided with a cylindrical centred through bore 32 and a cylindrical bore 34 of a larger diameter than the bore 32, the bore 34 extending from the first end portion 24 of the gauge housing 4 to a shoulder surface 36. In the bore 32 is placed a choke sleeve 40 provided with an external helical groove 38. The choke sleeve 40 has an axial, centred, threaded bore 42 extending therethrough. A seal 44 is disposed to encompass the external periphery of the choke sleeve 48 at the first end portion 24 of the gauge housing 4, and is arranged to prevent fluid leakage from the groove 38 to the first end portion 24 of the gauge housing 4. A seal 46 is sealingly placed between the choke sleeve 40 and the second end portion 20 of the flanged housing 2.

When the choke sleeve 40 is placed in the bore 34, the groove 38 of the choke sleeve 40 forms the first restriction 48 of the valve.

A threaded sleeve 50 extends in a displaceable and, by means of a seal 52, externally sealing manner within the bore 32 of the gauge housing 4, fitting complementarily into the treaded bore 42 of the choke sleeve 40, the threads of the threaded sleeve 50 forming, together with the threaded bore 42, an adjustable restriction 54, there being a relatively large clearance in said threaded connection. The adjustable restriction 54 is adjusted by the threaded sleeve 50 being screwed into/out of the threaded bore 42.

The threaded sleeve 50 is provided with an internal spline 56 complementarily matching the external spline of a splined shaft 58. At its one end portion, the splined shaft 58 is rotatably supported in a bearing 60 in the second end portion of the flanged housing 2, and is supported sealingly by means of a seal 62 at its opposite end portion, in a through bore 63 of the intermediate plate 6.

The splined shaft 58 is connected to a stepped motor 64 connected to the not shown monitoring and control unit of the valve 1. An inlet channel 66 connects the inlet coupling 12 to an annular space 68 defined by the threaded bore 42, the splined shaft 58, the end portion 20 of the flanged housing 2 and the threaded sleeve 50.

A connecting channel 70 extends through the choke sleeve 40 near the shoulder surface 36 from the threaded bore 42 to the external periphery of the choke sleeve 40. A first measuring channel 72 connects the bore 34 at the shoulder surface 36 to a first pressure sensor 74.

A second restriction 76 is disposed in an outlet channel 78 connecting the bore 34, in the area of that side of the seal 44, which faces the shoulder surface 36, to the outlet coupling 14. A second measuring channel 80 is connected to the outlet channel 78 between the bore 34 and the second restriction 76 and communicates with a second pressure sensor 82. A third measuring channel 84 connects the outlet channel 78 in the region between the second restriction 76 and the outlet coupling 14 to a third pressure sensor 86. The pressure sensors 74, 82 and 86 are connected through cables 88 to the not shown monitoring and control unit of the valve 1.

Both restrictions 48 and 76 are calibrated before application in order to determine the constant value R, exponent constant k for pressure drop and function f(v) for viscosity for each of the restrictions 48, 76.

In operation fluid flows from the inlet coupling 12 through the inlet channel 66 into the annular space 68. From the annular space 68 the fluid flows between the threaded bore 42 of the choke sleeve 40 and the threads of the threaded sleeve 50, together forming the adjustable restriction 54, further through the connecting channel 70 and then through the groove 38, the groove 38 forming, together with the bore 34, the first restriction 48. The fluid pressure within the connecting channel 70 propagates to the first manometer 74 through the first measuring channel 72.

From the first restriction 48 fluid flows by way of the outlet channel 78 through the second restriction 76 to the outlet coupling 14. The pressure within the outlet channel 78 between the first restriction 48 and the second restriction 76 propagates to the second pressure sensor 82 through the second measuring channel 80, whereas the pressure at the outlet coupling 14 propagates to the third pressure sensor 86 through the third measuring channel 84.

Figure 3:
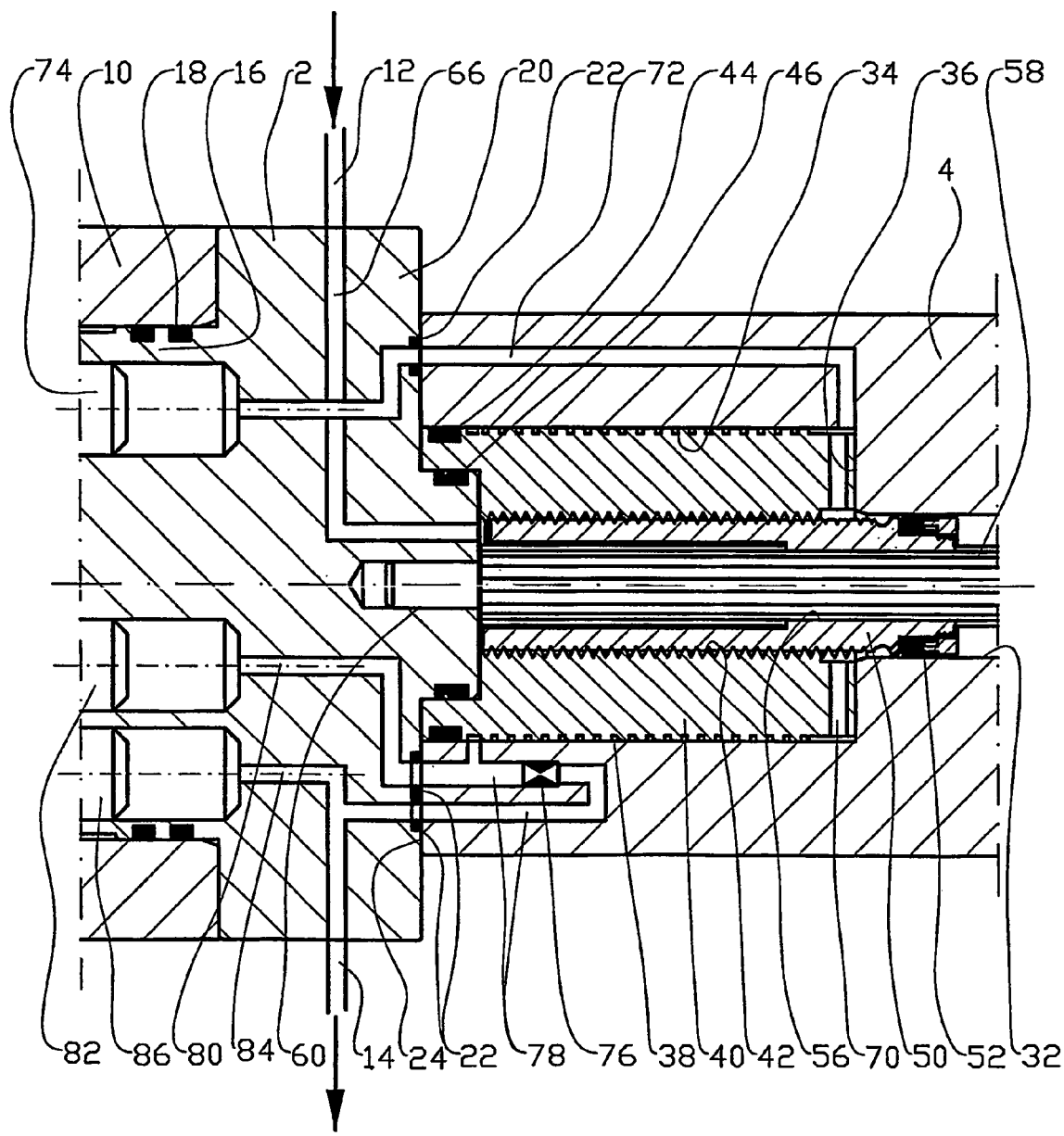
FIG. 3 shows the valve of FIG. 2 on a larger scale.

The amount of fluid flowing is adjusted in the adjustable restriction 54 by screwing the threaded sleeve 50 into/out of the threaded bore 42 until the desired pressure drop occurs across the first restriction 48. The screwing in/out of the threaded sleeve 50 is done by the stepped motor 64 rotating the splined shaft 58 and thereby the threaded sleeve 50 in a desired direction. The flow rate through the valve 1 is a known function of the difference between the fluid pressures measured in the first pressure sensor 74 and the second pressure sensor 82, based on calibration data for the first restriction 48 and the best viscosity value known. During the dosing of the flow rates involved here, the fluid flow is affected only to an insignificant degree by the second restriction 76, as the flow area of the second restriction 76 is relatively big to prevent clogging, for example by impurities in the fluid. In FIG. 3 the threaded sleeve 50 is in a position, in which there is a relatively great pressure drop across the adjustable restriction 54.

Figure 4:
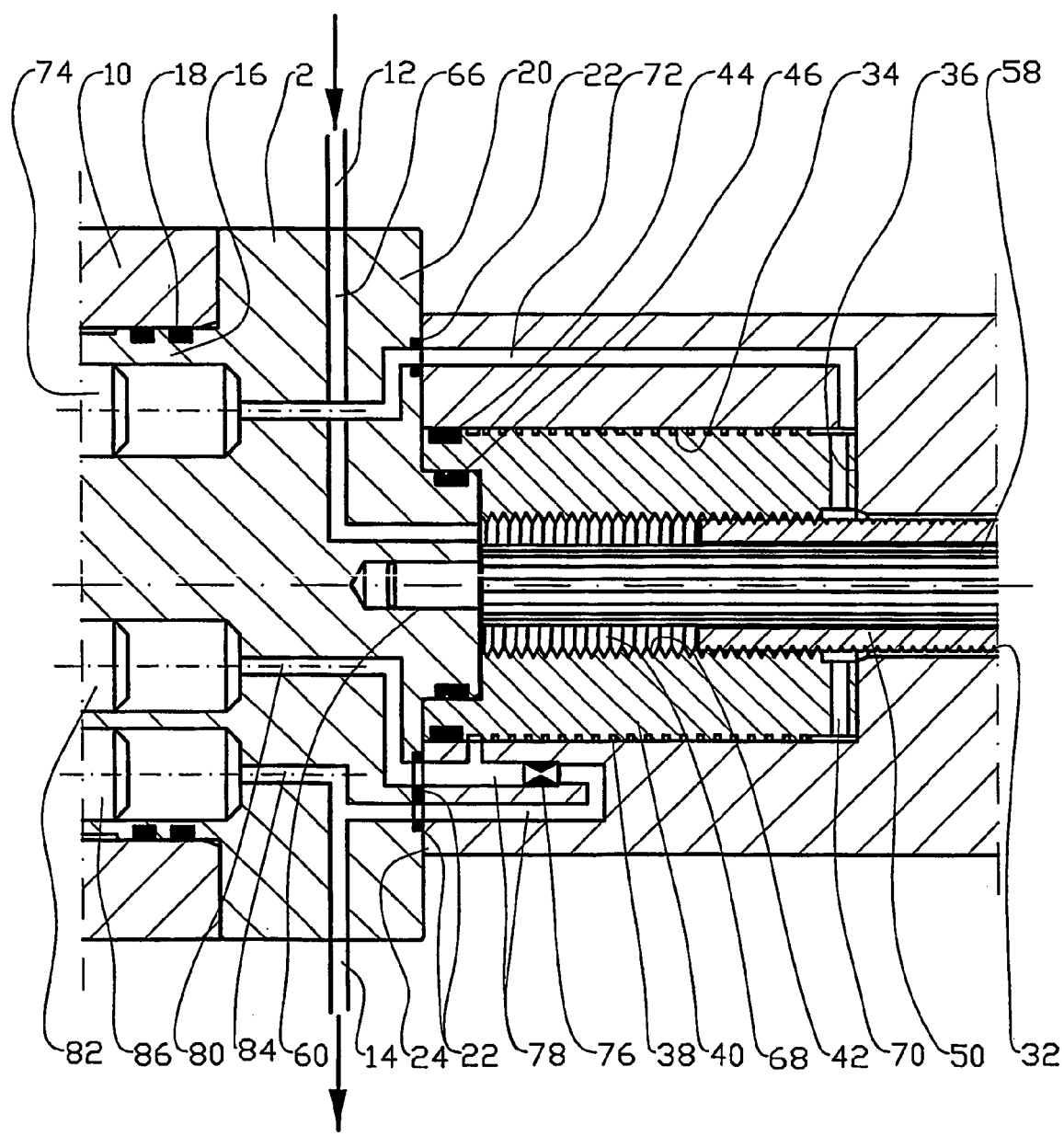
FIG. 4 shows the same as FIG. 3, but the adjustable choke valve has been opened to choke less and thereby allow a greater flow rate.

With the aim of determining the real viscosity of the fluid in the valve 1, the pressure drop in the adjustable restriction 54 is adjusted by the threaded sleeve 50 being screwed in a direction out of the threaded bore 42, see FIG. 4. The flow in the other restriction 76 will be adjustable by such a relatively great flow rate.

On the basis of pressure differences across the first restriction 48 and across the second restriction 76, appearing from the pressure values from the pressure sensors 74, 82 and 86, the viscosity of the fluid may be determined, as explained in the general part of the description.

The valve 1 is then adjusted until the desired flow rate is achieved, which is now calculated on the basis of the pertinent measured fluid viscosity.

If desirable, the valve may be provided with other measuring sensors, for example a temperature measuring device. Flow measuring valve 1 may be formed by a exchange unit.

The invention claimed is:

1. A flow measuring valve device (1) for the determination of the viscosity and flow rate of a fluid, where the fluid flows through a first restriction (48) and a second restriction (76) connected in series with the first restriction (48), the flow rates of said restrictions (48, 76) being unequally dependent on the viscosity of the fluid, characterized in that said restrictions (48, 76) are connected in series with a adjustable restriction (54).

2. A device according to claim 1, characterized in that the upstream sides and downstream sides of the first restriction (48) and second restriction (76) are connected to and able to communicate with respective pressure sensors (74, 82, 86).

3. A device according to claim 1, characterized in that the flow measuring valve (1) is disposed on the sea floor and is connected to and able to communicate with the surface.

4. A device according to claim 1, characterized in that the first restriction (48) of the flow measuring valve (1) is formed by a helical closed groove (38).

5. A device according to claim 1, characterized in that the adjustable restriction (54) of the flow measuring valve (1) is formed by a thread-like device (42, 50).

6. A device according to claims 5, characterized in that the thread-like device (42, 50) is arranged to be adjusted by means of a stepper motor (64) through a splined shaft (58).

7. A device according to claim 1, characterized in that the flow measuring valve (1) is formed by a remotely exchangeable unit.

8. A method for determining the viscosity of a fluid where the fluid flows through a first restriction (48) and a second restriction (76) connected in series with an adjustable restriction (54), the flow rates of said restrictions (48, 76) being unequally dependent on the viscosity of the fluid, and the constants of the restrictions (48, 76) being known as the pressure drop across each of the restrictions (48, 76) is being measured, characterized in that a viscosity, providing equal flow rate through both restrictions (48, 76), is deduced by means of iteration with respect to the viscosity of the fluid.

9. A method according to claim 8, characterized in that the continuity equation for the flow of the fluid in series through the first restriction (48) and the second restriction (76) is solved.

\* \* \* \* \*